(12) United States Patent
Beerling et al.

(10) Patent No.: US 8,501,029 B2
(45) Date of Patent: Aug. 6, 2013

(54) MICROMACHINED TITANIUM FOR HIGH PRESSURE MICROFLUIDIC APPLICATIONS

(75) Inventors: Timothy Beerling, San Francisco, CA (US); Hongfeng Yin, Cupertino, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 918 days.

(21) Appl. No.: 11/554,537

(22) Filed: Oct. 30, 2006

(65) Prior Publication Data

US 2008/0142479 A1 Jun. 19, 2008

(51) Int. Cl.
*C23F 1/00* (2006.01)

(52) U.S. Cl.
USPC .......................................................... 216/96

(58) Field of Classification Search
USPC ............ 210/635, 656, 198.2; 435/6; 216/96, 216/75, 74; 156/272; 420/68; 422/100, 422/99
See application file for complete search history.

(56) References Cited

U.S. PATENT DOCUMENTS

| | | | | |
|---|---|---|---|---|
| 4,362,598 A | * | 12/1982 | Griffing | 216/57 |
| 4,863,550 A | * | 9/1989 | Matsuo et al. | 156/353 |
| 4,890,784 A | * | 1/1990 | Bampton | 228/194 |
| 5,393,375 A | | 2/1995 | MacDonald et al. | |
| 5,492,555 A | * | 2/1996 | Strunk et al. | 95/86 |
| 5,500,071 A | | 3/1996 | Kalentbach et al. | |
| 5,756,237 A | | 5/1998 | Amemiya | |
| 5,831,252 A | * | 11/1998 | Shimizu | 219/603 |
| 5,972,369 A | * | 10/1999 | Roorda et al. | 424/424 |
| 6,054,384 A | * | 4/2000 | Wang et al. | 438/637 |
| 6,444,138 B1 | * | 9/2002 | Moon et al. | 216/79 |
| 6,548,895 B1 | * | 4/2003 | Benavides et al. | 257/712 |
| 6,993,958 B2 | * | 2/2006 | Paul | 73/54.05 |
| 2001/0047961 A1 | * | 12/2001 | Gjerde et al. | 210/635 |
| 2004/0207074 A1 | * | 10/2004 | MacDonald et al. | 257/708 |
| 2005/0109240 A1 | * | 5/2005 | Maeta et al. | 106/493 |
| 2005/0223775 A1 | * | 10/2005 | Klee et al. | 73/23.41 |

OTHER PUBLICATIONS

Wei Heong Tan et al , PNAS, vol. 104(2007)1146-1151.*
Yanting Zhang, "Bulk Titanium Microfluidic Devices", PhD Dissertation, University of California, Santa·Barbara, Mar. 2006 Holger Becker, " Polymer Microfluidic Devices", Talanta, vol. 56(2002)267-287.*
Heckele et. al.,"replication and bonding techniques for integrated microfluidic systems", Microsystems Technology, 12(Jun. 2006)1031-1035.*
Yanting Zhang, "Bulk Titanium Microfluidic Devices", PhD Dissertation, University of California, Santa Barbara, Mar. 2006 Holger Becker, "Polymer Microfluidic Devices", Talanta, vol. 56(2002)267-287.*
E. R. Parker, et. al. Inductively Coupled Plasma Etching of Bulk Titanium for MEMS Applications, Journal of Electrochemical Society, 152(2005) C675.*
Timothy A. Fofonoff,"Microelectrode Array Fabrication by Electrical Discharge Machining and Chemical etching", IEEE Transactions on Biomedical Engineering, vol. 51(2004)890.*
Heckele et. al.,"replication and bonding techniques for integrated microfluidic systems", Microsystems Technology, 12( Jun. 2006)1031-1035.*

* cited by examiner

*Primary Examiner* — Michael Cleveland
*Assistant Examiner* — Tabassom Tadayyon Eslami

(57) ABSTRACT

In accordance with the invention, a method for making microfluidic structures in bulk titanium is disclosed. Specific microfluidic structures include HPLC structures.

22 Claims, 17 Drawing Sheets

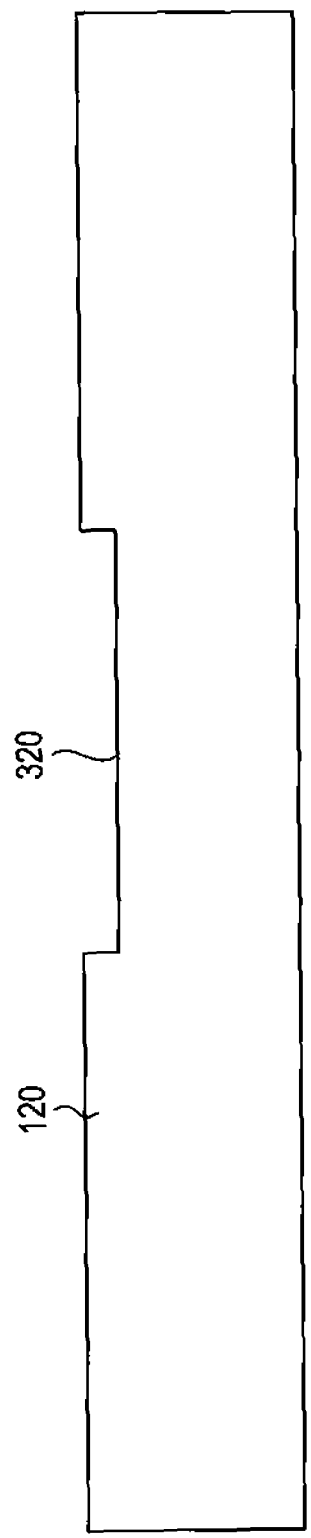

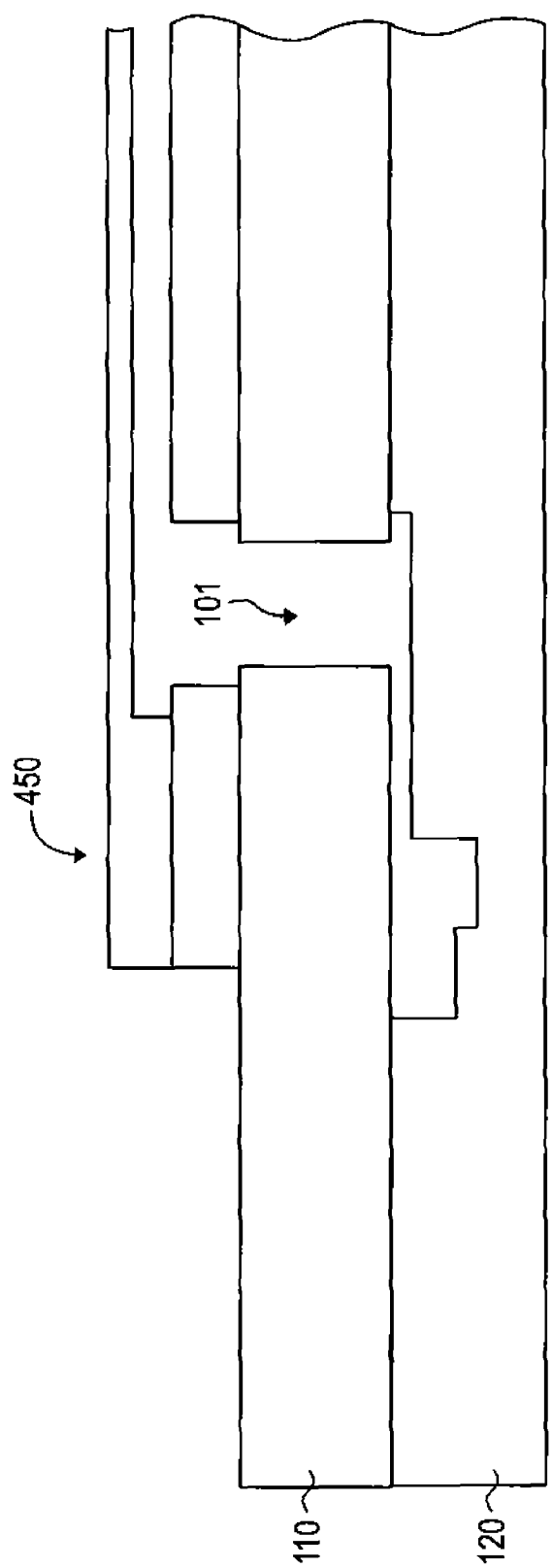

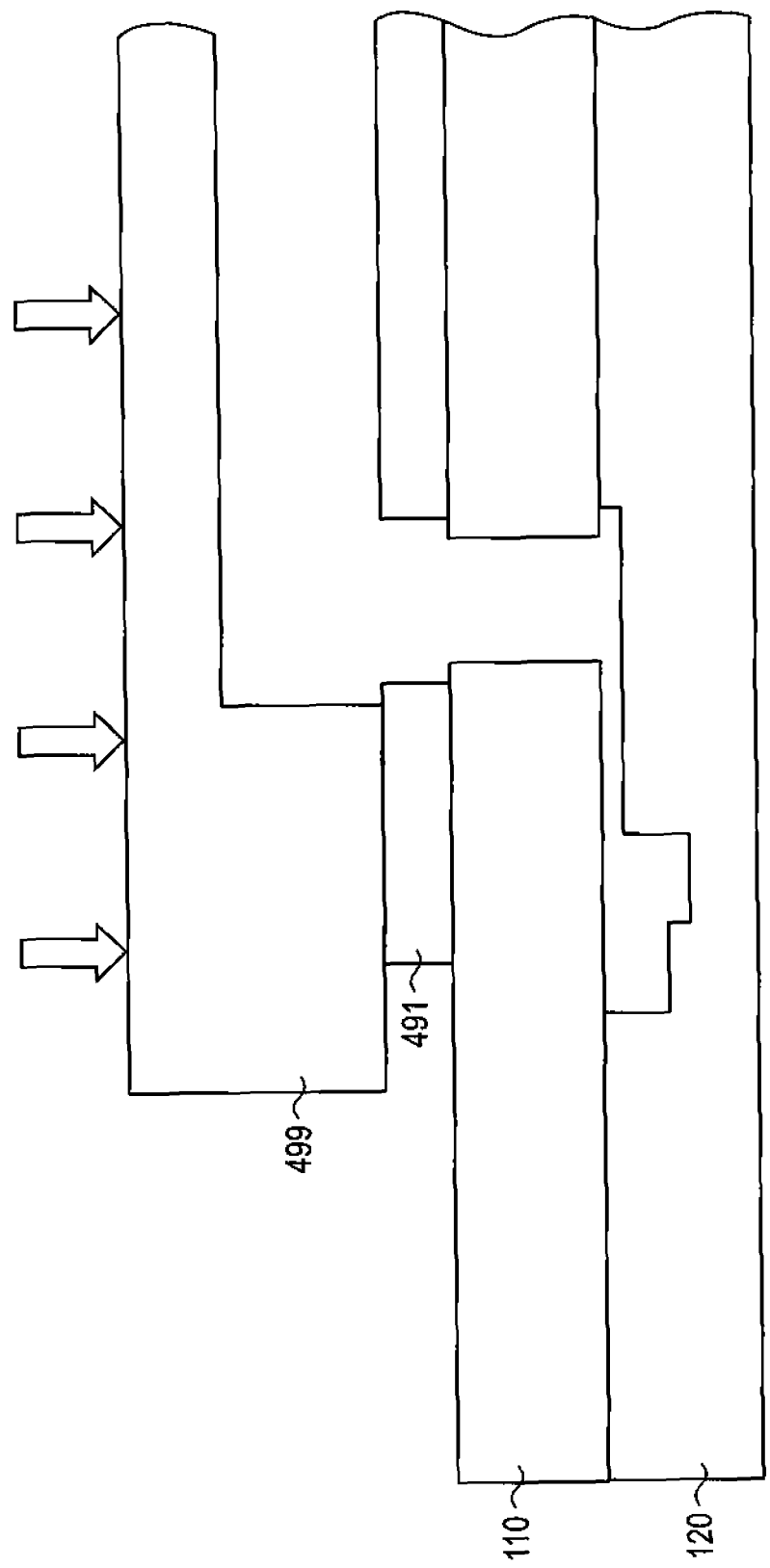

MICROMACHINED TITANIUM FOR HIGH PRESSURE MICROFLUIDIC APPLICATIONS

BACKGROUND

Microfluidic applications sometimes require high pressure operation such as in the area of high performance liquid chromatography (HPLC). Microfluidic chips with integrated HPLC columns such as described in U.S. Pat. No. 5,500,071, incorporated herein by reference, have become popular in mass spectrometer applications. Typically, micromachined polymer columns are used for integrated HPLC columns, typically comprising two to five micromachined polymer sheets. However, the upper limits on pressure for typical polymer materials may limit their use for some application areas. Replacing typical polymer materials with type 304 stainless steel allows significantly higher pressure applications but type 304 stainless steel typically does not have the comparatively good micromachining techniques that titanium has associated with it.

SUMMARY

In accordance with the invention, a method for making microfluidic structures in bulk titanium is disclosed. Specific microfluidic structures include HPLC structures.

BRIEF DESCRIPTION OF THE DRAWINGS

FIGS. 4a-4k show embodiments in accordance with the invention.

DETAILED DESCRIPTION

A material that has mechanical properties significantly better than typical polymers and similar to type 304 stainless steel is titanium (commercially pure titanium, grade 2). Commercially pure titanium comes in many grades, and has impurities such as oxygen, carbon and iron, at a total concentration of about one percent or less. Table 1 shows a comparison of mechanical properties of typical grade 2 titanium and type 304 stainless steel. Grade 2 titanium is typically readily available commercially in thin sheet form. Other commercially pure grades of titanium have superior mechanical properties with respect to grade 2, such as grade 4 titanium.

TABLE 1

|  | Titanium, CP grade 2 | Type 304 Stainless Steel |
| --- | --- | --- |
| Density | 4510 kg/m$^3$ | 8250 kg/m$^3$ |
| Elastic Modulus | 105 GPa | 193 GPa |
| Poisson's Ratio | 0.37 | 0.29 |
| Tensile Strength | 430 MPa | 515 MPa |
| Thermal Expansion Coefficient | 8.9 × 10$^{-6}$/° K | 17.2 × 10$^{-6}$/° K |
| Vickers-Hardness | 145 | 129 |

Additionally, titanium typically allows for comparatively good micromachining techniques and is typically bio-compatible. Like type 304 stainless steel, titanium allows diffusion bonding to create multilayer structures from sheets as thin as 1-2 mils. Titanium diffusion bonding is typically carried out at temperatures greater than about 750° C. but needs to be below the hexagonal closed packed (HCP) to body centered cubic (BCC) transition if fine features are to be maintained. This transition temperature typically varies with the amount of impurities but is about 883° C. for pure titanium. Pressure during bonding are typically in the range from about 10 atms to about 500 atms.

Figure 1A:
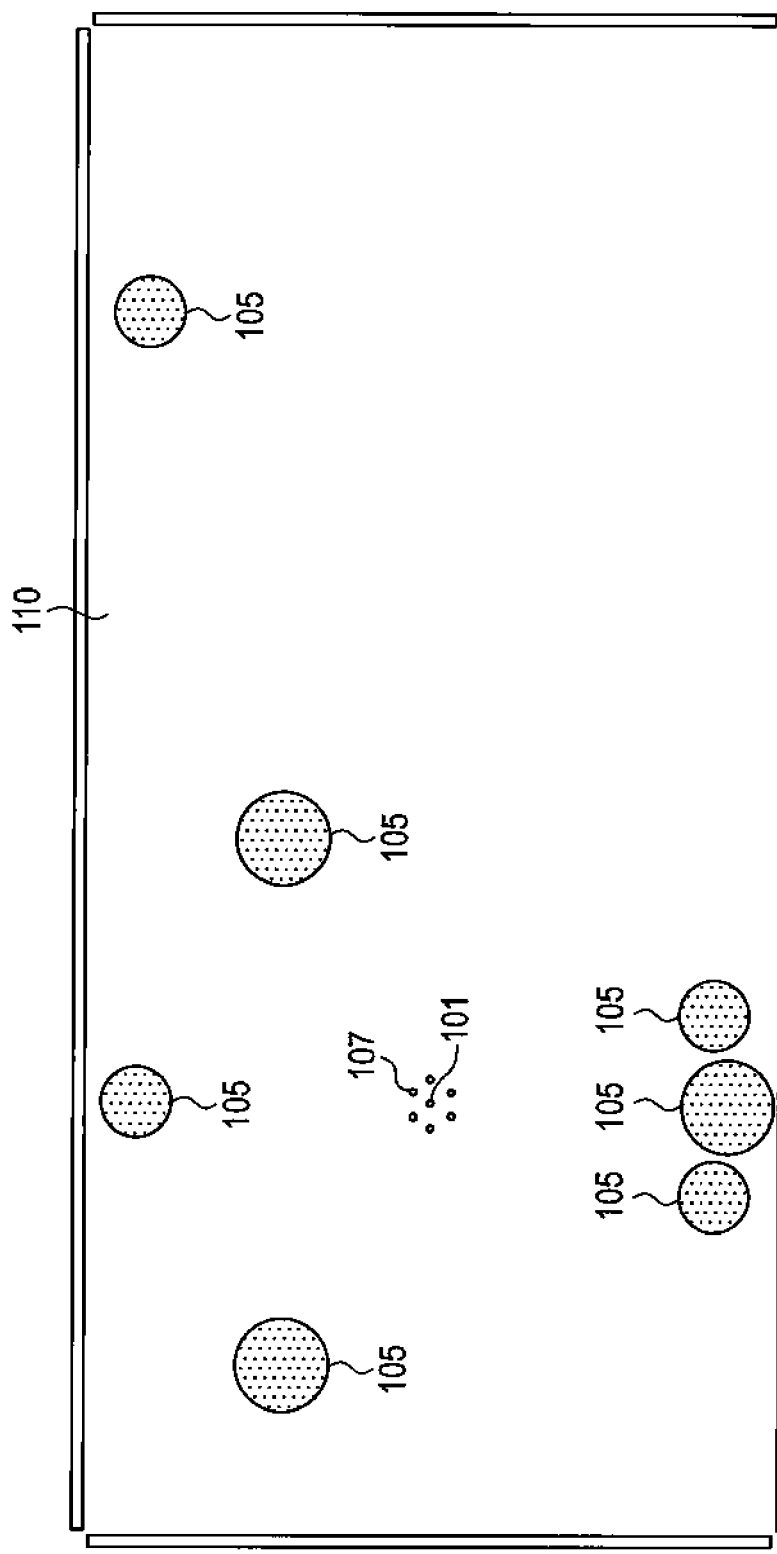
FIGS. 1a-b show an embodiment in accordance with the invention.
Figure 1B:
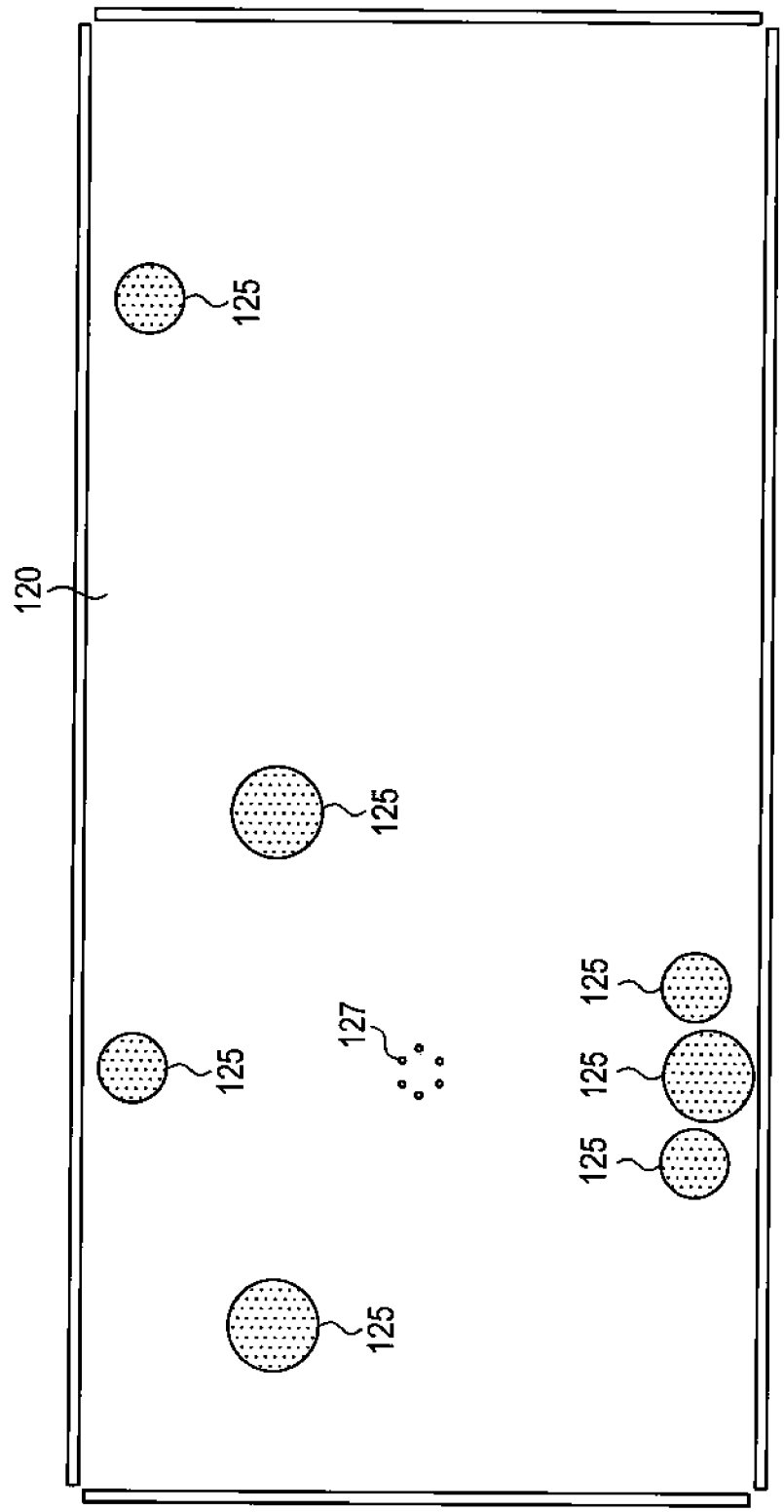

As seen from the above, titanium is an attractive material for certain high pressure microfluidic applications. In particular, an exemplary embodiment in accordance with the invention is the making of integrated HPLC columns for use in microfluidic chips. FIGS. 1a and 1b show titanium sheet 110 and titanium sheet 120, respectively, for making an integrated HPLC column. FIG. 1a shows alignment holes 105 along with fluidic input/output holes 107 along with optional hole 101 for connection to an electrospray head or ultraviolet (UV) detection cell. FIG. 1b shows alignment holes 125 along with fluidic input/output holes 127 in titanium sheet 120. Holes 105, 107, 125 and 127 are typically created using electrical discharge machining (EDM) in accordance with the invention. EDM is a technique typically used for hard metals that are electrically conductive. EDM is a nontraditional method of removing material using a series of rapidly recurring electric arcing discharges between an electrode and a work piece such as titanium sheets 110 and 120, in the presence of an energetic electric field. Other methods in accordance with the invention for making holes 105, 107, 125 and 127 include punching, laser machining and water jet.

Titanium sheets 110 and 120 are typically commercially pure grade 1-4 or grade 7 and are typically machined and polished prior to their use. Optionally, titanium sheets 110 and 120 may be cleaned to remove machining damage and machine oils by using an acid such as 25% HCL at elevated temperatures which removes titanium in the surface region. Surface roughness is typically less than a few micrometers (Ra). Typical thicknesses for titanium sheets 110 and 120 are in the range from about 50 micrometers to about 500 micrometers.

Figure 2:
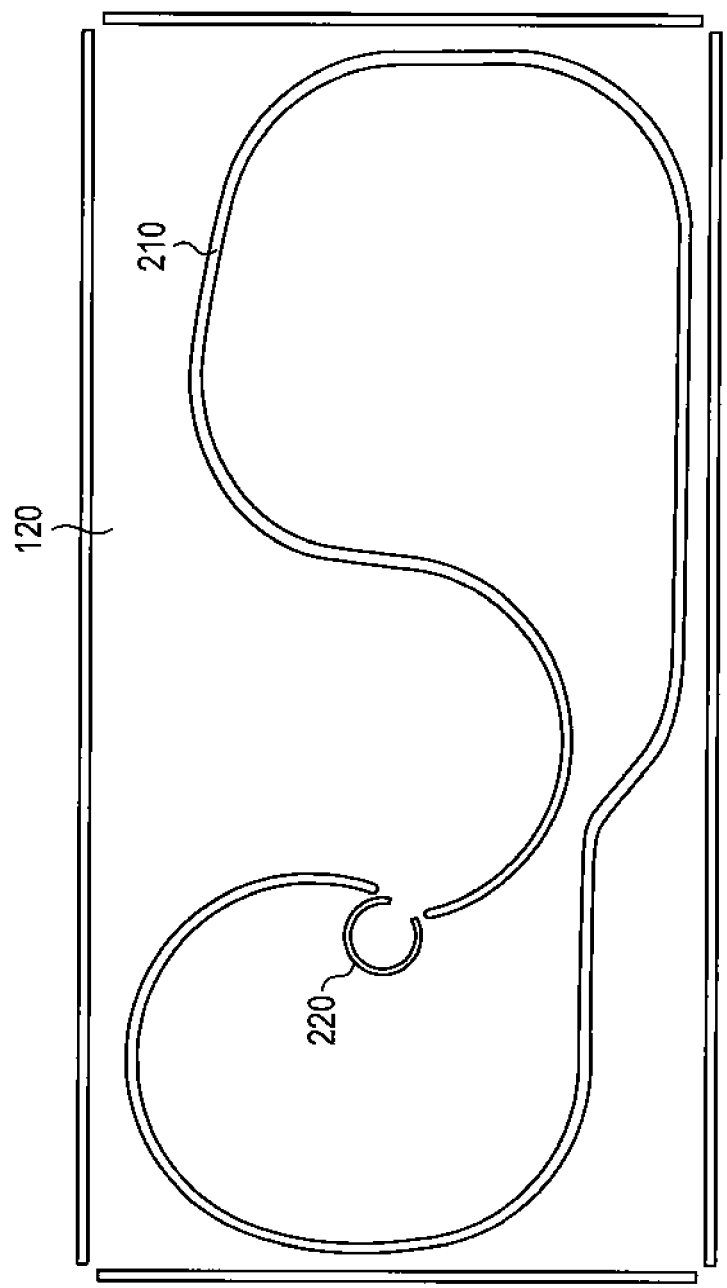
FIG. 2 shows a microfluidic structure in accordance with the invention.
Figure 3:
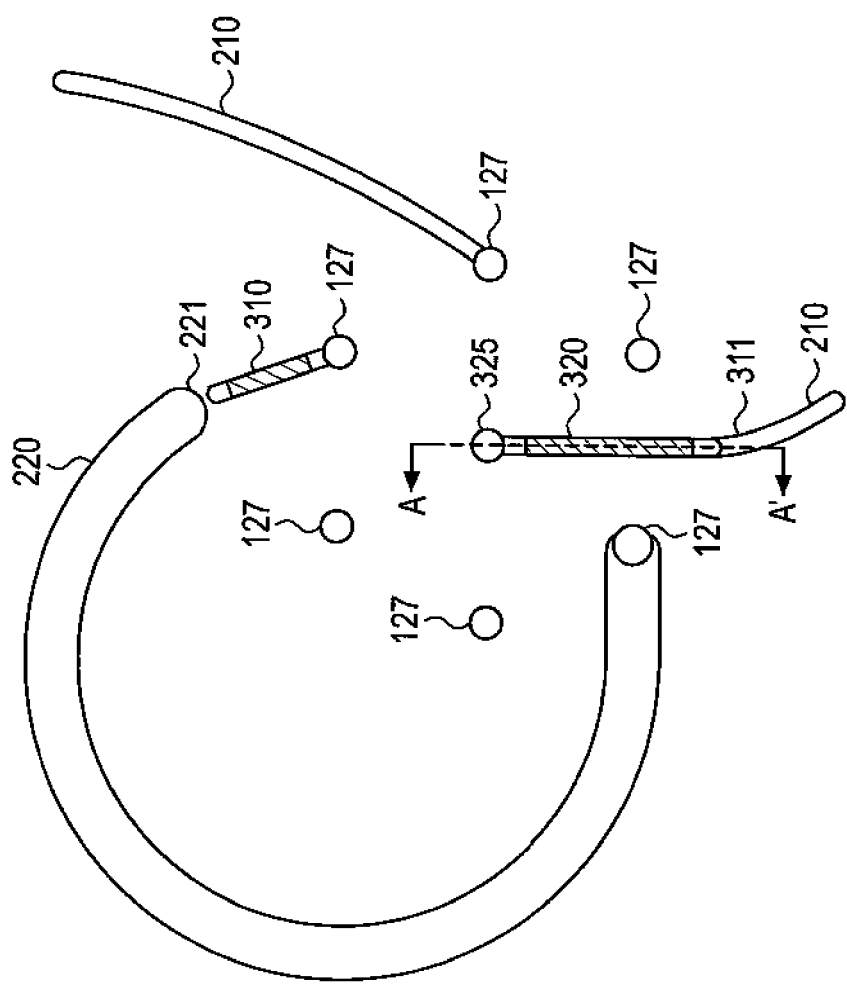
FIG. 3 shows a microfluidic structure in accordance with the invention.

FIG. 2 shows titanium sheet 120 with the layout for masks for separation column 210 and enrichment column 220. Deep reactive ion etching (DRIE) is typically used to define separation column 210 and enrichment column 220 in titanium sheet 120 in accordance with the invention. FIG. 3 shows a close up in the vicinity of enrichment column 220 and fluidic input/output holes 127 in titanium sheet 120. Bead trap 310 is fluidically coupled to enrichment column end 221 while bead trap 320 is fluidically coupled to separation column end 311. Bead traps 310 and 320 are typically etched using reactive ion etching (RIE) and are not etched as deeply as enrichment column 220 or separation column 210. The etched feature 325 aligns with through-hole 101 in titanium sheet 110 for fluidic coupling to an electrospray head or ultraviolet detection cell.

Figure 4A:
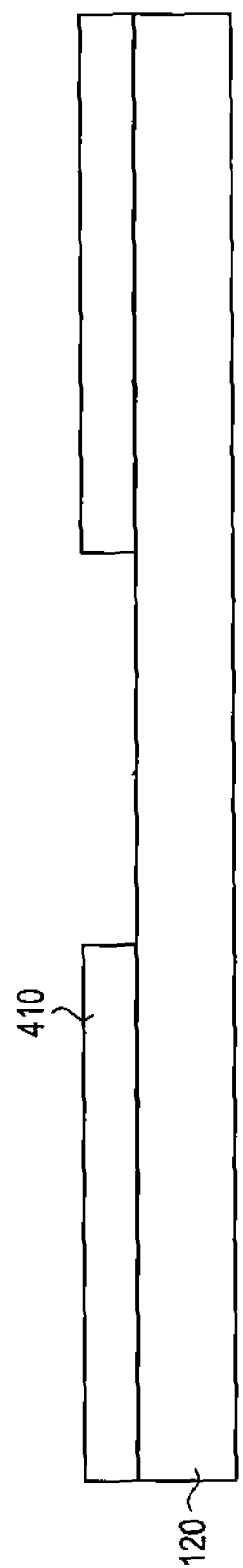

FIGS. 4a-4i show the processing steps for titanium sheets 120 and 110 in an embodiment in accordance with the invention for a representative cross-section along line AA' in FIG. 3. Initially, photoresist layer 410 is spun onto titanium sheet 120 and patterned using standard techniques. FIG. 4a shows titanium sheet 120 with patterned photoresist layer 410 for a shallow RIE etch.

FIG. 4b shows the result of the shallow RIE etch to create beadtrap 320 which typically has a depth less than about 10 micrometers. Photoresist layer 410 is typically removed using hot solvents or basic solutions.

Figure 4C:
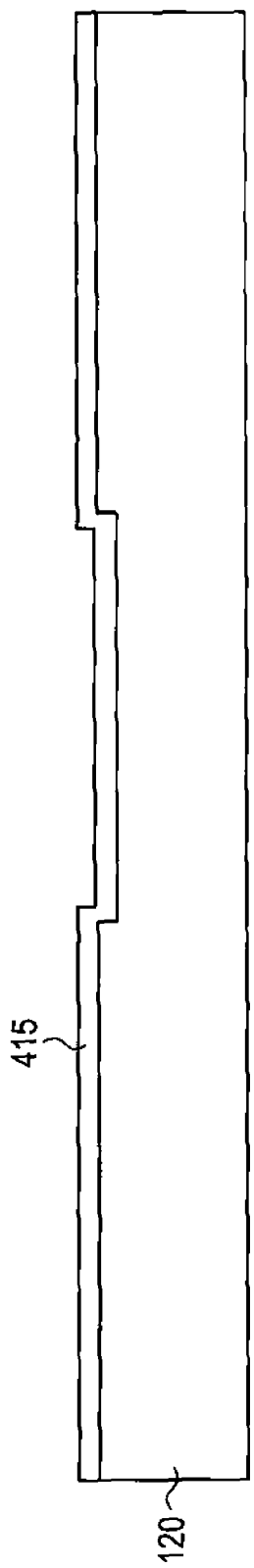
Figure 4D:
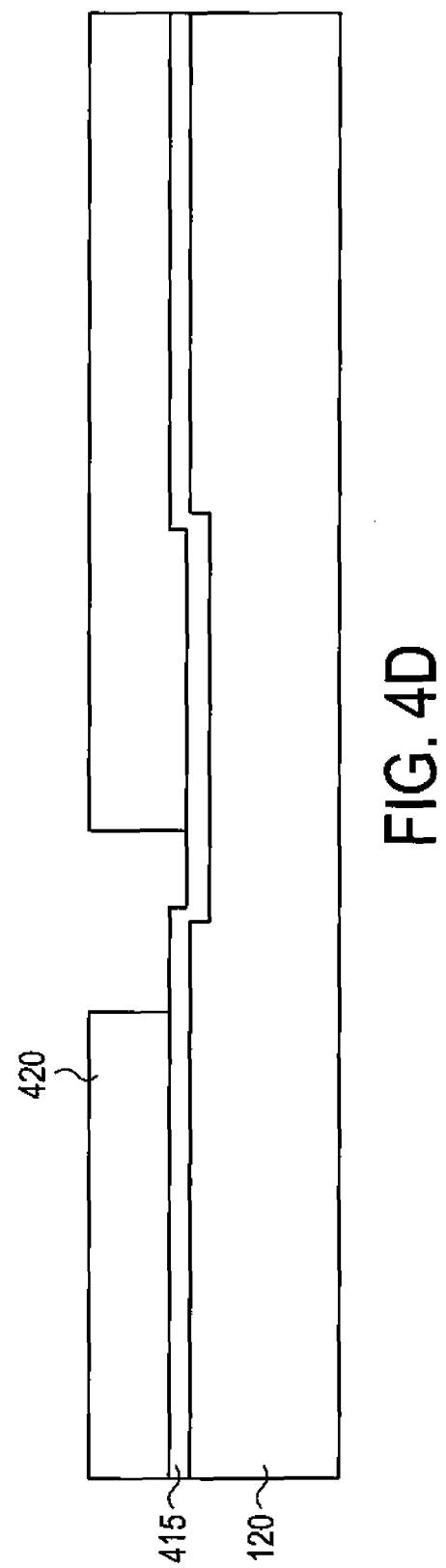
Figure 4E:
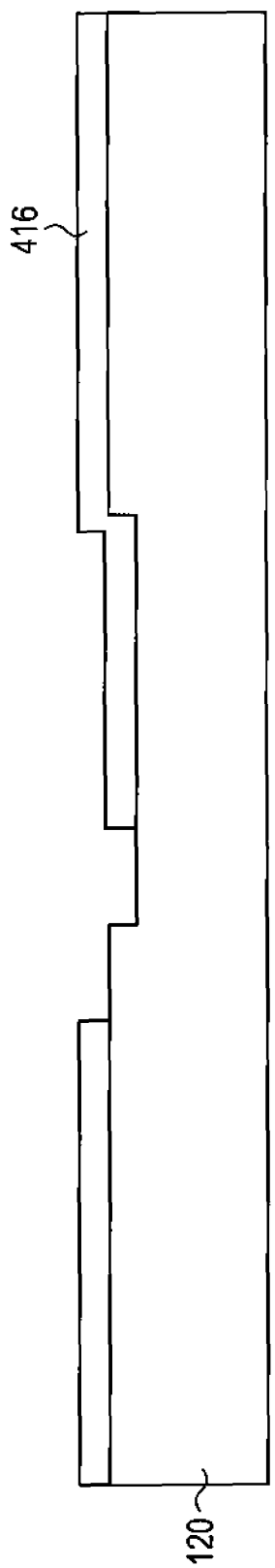
Figure 4F:
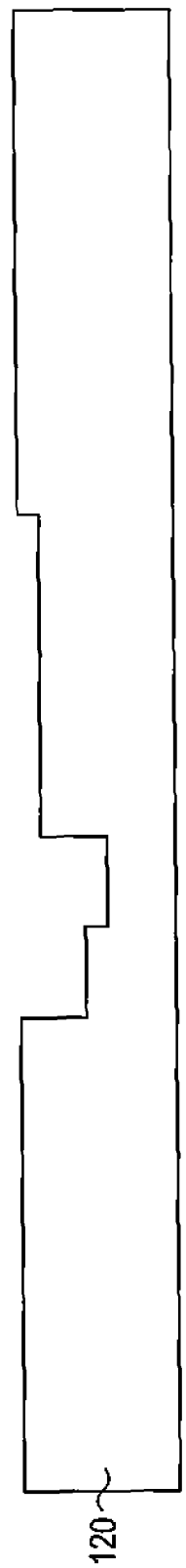

FIG. 4c shows deposition of hard mask 415 which is typically reactively sputtered to thicknesses in the range from about 1 micrometer to about 5 micrometers onto titanium sheet 120 in preparation for a deep RIE (DRIE) etch. Typical materials for hard mask 415 are tantalum oxide ($Ta_2O_5$) or titanium oxide ($TiO_2$), but other chlorine resistant materials may be used for hard mask 415. FIG. 4d shows patterned photoresist layer 420 which is used to provide a pattern on hard mask 415 to create patterned hard mask 416. DRIE is then performed on hard mask 415 to pattern hard mask 415. After the DRIE is complete, photoresist layer 420 is removed using hot solvents or basic solutions resulting in the intermediate structure shown in FIG. 4e.

Typically a chlorine-based or chlorine-boron trichloride mixture based DRIE etch is then used to etch titanium sheet 120 using patterned hard mask 416. For the chlorine-based DRIE etch, an inductively coupled plasma (ICP) etcher is used with additional radio frequency (RF) power applied at the platen. The power applied to the ICP etcher is typically in the range from about 500 W to about 2000 W while the RF power applied at the platen is typically in the range from about 50 W to about 500 W. Pressure in the reactor is typically in the range from about 5 mTorr to about 50 mTorr with either $Cl_2$ or a mixture of $Cl_2/BCl_3$ supplied at a gas flow rate typically greater than 20 sccm. Total flow rates of over 100 sccm may be required because the etch rate is dependent on the halogen flow rate. If another DRIE etch is required, a photoresist layer can be applied to further pattern patterned hard mask 416. Depending on the ordering of etch steps it may be necessary to remove patterned hard mask 416 and reapply hard mask 415 between DRIE steps. If photoresist "speedboating" becomes an issue, the conductive properties of titanium allow the deposition of electroplated resist which is highly conformal. After completion of the chlorine-based DRIE etch, patterned hard mask 416 is removed using fluorine based dry etch chemistries, with better selectivity for removing patterned hard mask 416, resulting in the intermediate structure shown in FIG. 4f. Alignment holes 105 and 125, respectively, along with fluidic input/output holes 107 and 127, respectively, are typically made using EDM. If desired, optional hole 101 is also created typically using EDM for connecting to polymer microfluidic circuit 450 (see FIG. 4i).

Figure 4G:
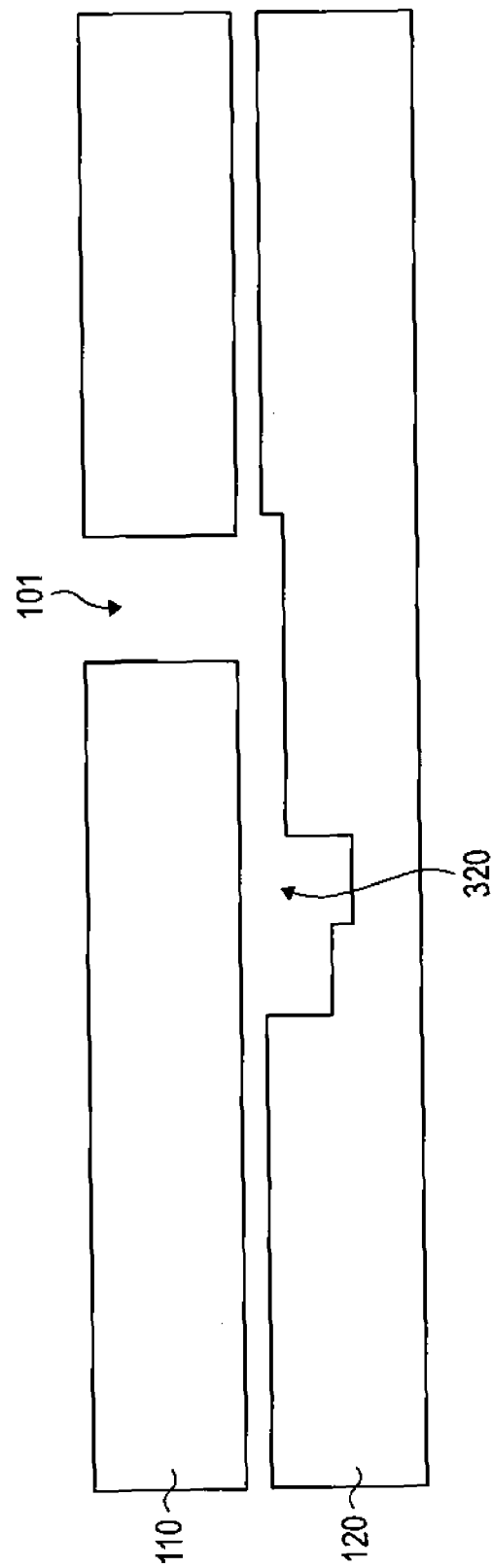

In FIG. 4g, titanium sheets 110 and 120 are brought together. After titanium sheets 110 and 120 are properly aligned, using alignment features on the titanium disk, but outside the chip area, taking care that fluidic input/output holes 107 and 127 are properly aligned with one another, titanium diffusion bonding is performed to bond titanium sheets 110 and 120 together. Typically, titanium diffusion bonding is performed by specialists, such as, for example, REFRAC SYSTEMS of Chandler, Ariz. Note that multilayer structures may require polishing after diffusion bonding has been performed. Typical temperatures for titanium bonding are greater than about 750° C. but the bonding temperature needs to be kept below the HCP to BCC transition temperature which depends on the amount of impurities in the titanium but is about 883° C. for pure titanium. Pressures typically used for titanium bonding are in the range from about 10 atms to about 350 atms.

Figure 4H:
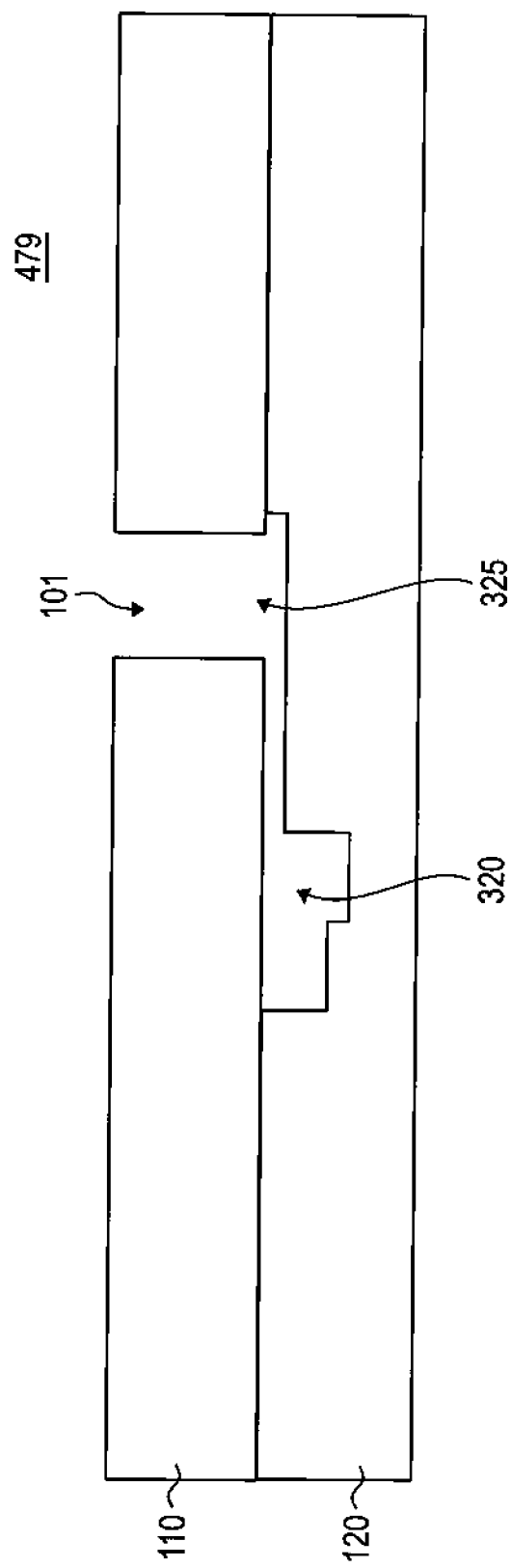
Figure 4J:
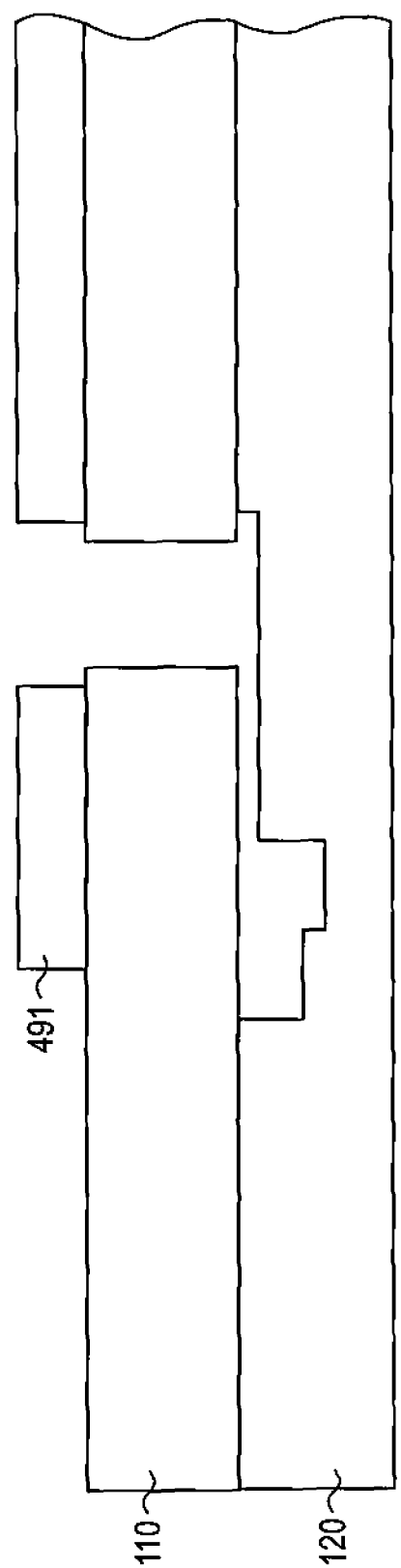

FIG. 4h shows the cross-section of HPLC column structure 479 along line AA' after titanium sheets 110 and 120 have been bonded together. Singulation is then performed to create the individual HPLC column structures 479 using traditional cutting techniques or possibly DRIE. Optionally, polymer microfluidic circuit 450 may be attached to HPLC column structure 479 for attachment of an electrospray nozzle as shown in FIG. 4i. Some surface roughness on titanium sheet 110 may assist in the adhesion of polymer microfluidic circuit 450 to titanium sheet 110. Note that polymer microfluidic circuit 450 is at comparatively low pressure because it lies downstream from separation column 210.

FIG. 4k shows another option for attaching ultraviolet (UV) cell 499 to HPLC column structure 479. Polymer based layer 491 is laser machined and laminated to titanium sheet 110, functioning as a gasket. Any laminable, soft, and biocompatible material may be used, however. In FIG. 4k, UV cell 499 is press fit onto polymer based layer 491 during operation, as shown.

Figure 5:
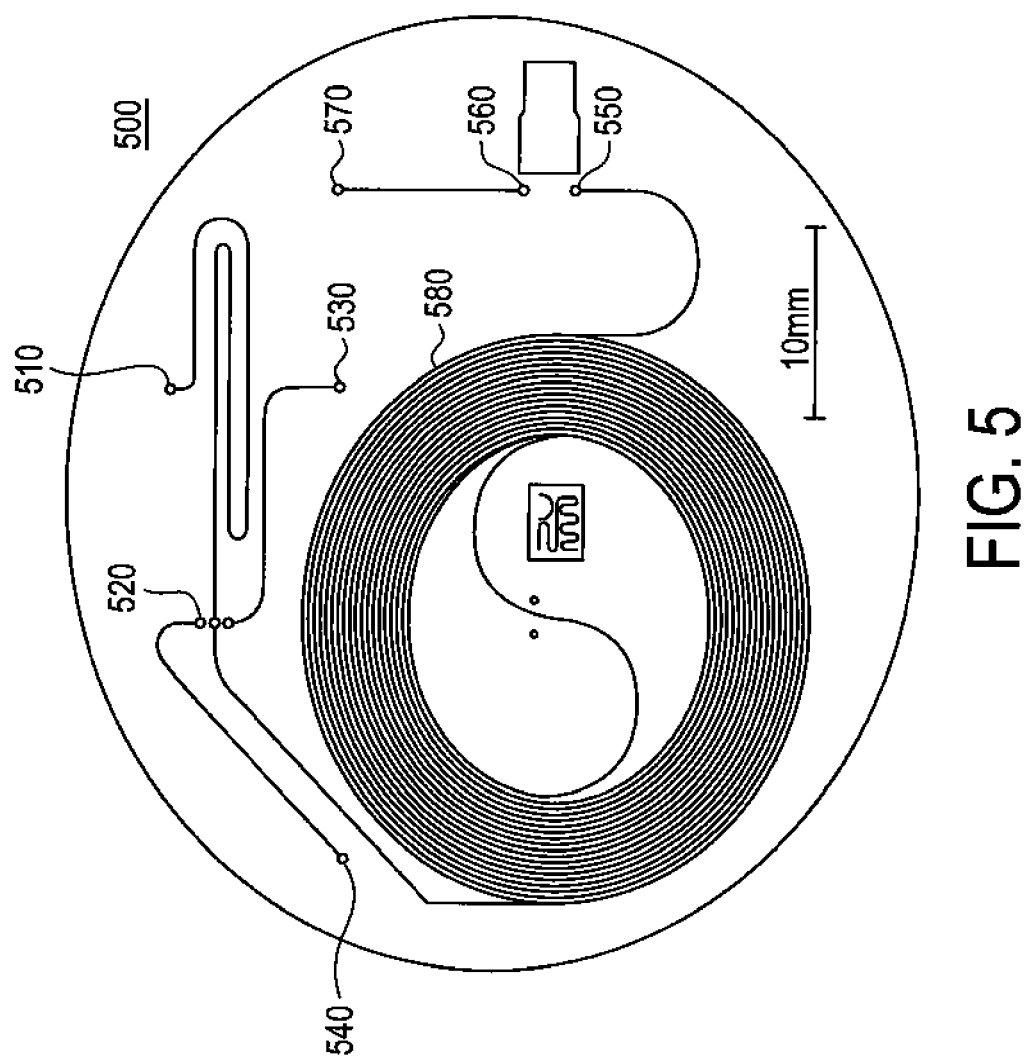
FIG. 5 shows a microfluidic structure in accordance with the invention.

In accordance with the invention, other microfluidic structures may similarly be made on titanium substrates. For example, FIG. 5 shows gas chromatograph system 500. Features include carrier gas input 510, feedthrough holes 520, sample gas input 530 sample gas output 540, feedthrough holes 550 and 560 to detector, carrier gas vent to atmosphere 570 and spiral capillary column 580. These features may be etched into a titanium sheet with a second titanium sheet suitably patterned being bonded over the first titanium sheet.

Figure 6:
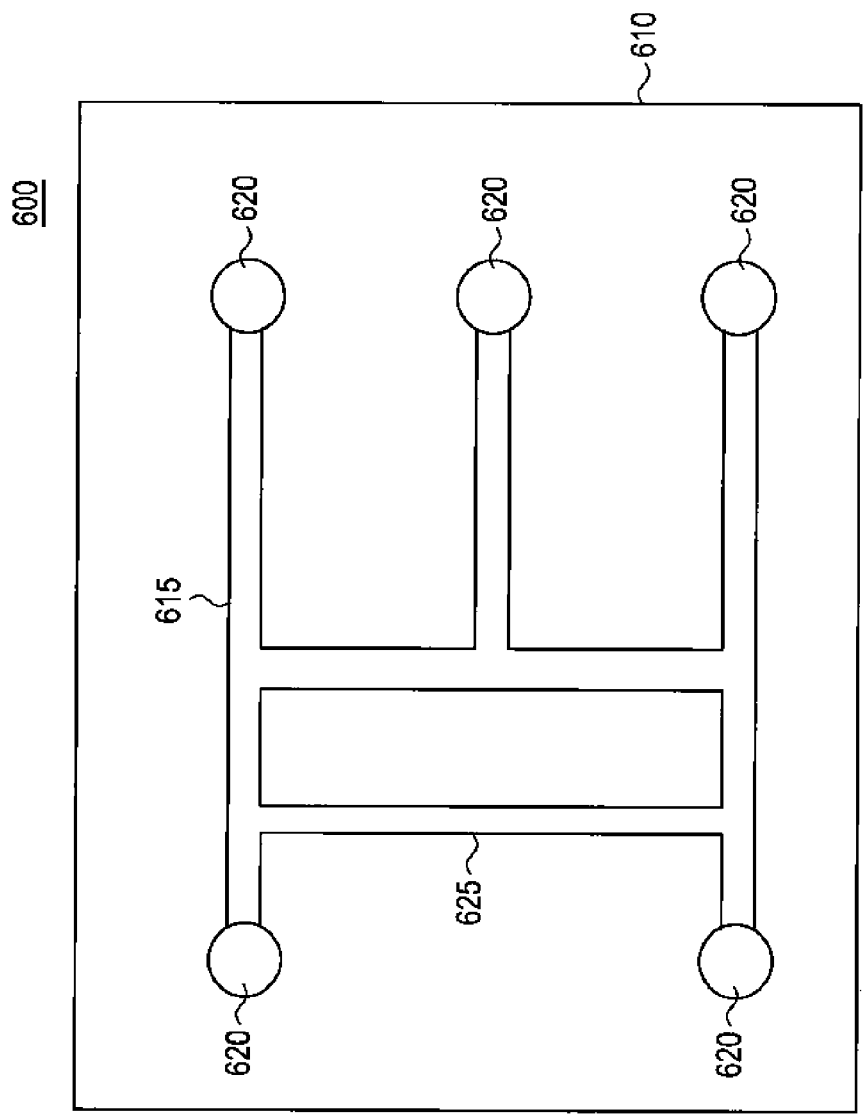
FIG. 6 shows a microfluidic structure in accordance with the invention.

Another example is a Dean's switch which can advantageously be etched in a titanium substrate in accordance with the invention as this allows better feature definition allowing lower gas flowrates while allowing higher temperatures. FIG. 6 shows an exemplary embodiment of Dean's switch 600 in titanium plate 610. In accordance with the invention, microfluidic channels 615 and shunt restrictor 625 are etched in titanium substrate 610 as shown, along with ferrule alignment structures 620. Typical width dimensions for microfluidic channels 615 are in the range from about 75 micrometers to about 100 micrometers while the width dimension for shunt restrictor 625 is on the order of about 20 micrometers. A top titanium plate with through holes (not shown) for the ferrules that are aligned with ferrule alignment structures 620 is diffusion bonded to titanium plate 610. The through holes are typically created using electrical discharge machining (EDM) in accordance with the invention. Dean's switch 600 may also be integrated with other microfluidic structures on titanium plate 610.

While the invention has been described in conjunction with specific embodiments, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

The invention claimed is:

1. A method for creating a microfluidic column in a titanium substrate, the method comprising:
   depositing a hard mask layer on said titanium substrate;
   masking said hard mask layer with a photoresist layer;
   patterning said photoresist layer;
   performing an RIE etch on said masked hard mask layer to form a hard mask patterned with a shape of said microfluidic column, the shape comprising arcuate portions along a length of the hard mask layer;
   and
   etching through said hard mask and into but not through said titanium substrate using a DRIE etch to form said microfluidic column comprising the arcuate portions alone a length of the microfluidic column.

2. The method of claim 1 wherein said DRIE etch is selected from the group consisting of a chlorine-based DRIE etch and a chlorine-boron trichloride mixture based DRIE etch.

3. The method of claim 1 further comprising removing said patterned hard mask using fluorine based dry etch chemistries.

4. The method of claim 1 wherein said DRIE etch comprises using an inductively coupled plasma etcher with additional radio frequency power applied to a platen.

5. The method of claim 1 wherein said microfluidic structure comprises a Dean's switch.

6. The method of claim 1 wherein said microfluidic structure comprises a capillary column.

7. The method of claim 1 further comprising:
providing a titanium sheet; and
attaching said titanium sheet to said titanium substrate using diffusion bonding.

8. The method of claim 7 further comprising forming alignment holes through said titanium sheet.

9. The method of claim 8 wherein said forming comprises electrical discharge machining.

10. The method of claim 7 wherein said titanium sheet is acid cleaned prior to said diffusion bonding.

11. The method of claim 7 wherein said diffusion bonding is performed at a temperature greater than about 750° C. but less than about 883° C.

12. A method for creating an integrated high pressure liquid chromatograph (HPLC) column in a titanium substrate, the method comprising:
depositing a hard mask layer on said titanium substrate;
applying a photoresist layer onto said hard mask layer;
patterning said photoresist layer;
performing an RIE etch on said masked hard mask layer to form a hard mask patterned with a shape of said integrated HPLC column, the shape comprising arcuate portions along a length of the hard mask layer;
and
etching through said hard mask and into but not through said titanium substrate using a DRIE etch to form said HPLC column comprising the arcuate portions along a length of the HPLC column.

13. The method of claim 12 further comprising removing said patterned hard mask using fluorine based dry etch chemistries.

14. The method of claim 12 wherein said DRIE etch is selected from the group consisting of a chlorine-based DRIE etch and a chlorine-boron-trichloride mixture based DRIE etch.

15. The method of claim 12 further comprising:
spinning a first photoresist layer on said titanium substrate;
patterning said first photoresist layer; and
performing a shallow RIE etch to create a beadtrap.

16. The method of claim 12 wherein said integrated HPLC structure comprises a microfluidic structure selected from the group consisting of a separation column and an enrichment column.

17. The method of claim 12 further comprising:
providing a titanium sheet; and
attaching said titanium sheet to said titanium substrate using diffusion bonding.

18. The method of claim 17 wherein a polymer based layer is laminated on said titanium sheet to accommodate attachment of an ultraviolet cell.

19. The method of claim 17 wherein said titanium sheet is acid cleaned prior to said diffusion bonding.

20. The method of claim 17, further comprising forming alignment holes through said titanium sheet.

21. The method of claim 20 wherein said forming comprises electrical discharge machining.

22. The method of claim 12 wherein a polymer microfluidic circuit is attached to said integrated HPLC structure.

* * * * *

UNITED STATES PATENT AND TRADEMARK OFFICE
CERTIFICATE OF CORRECTION

PATENT NO. : 8,501,029 B2
APPLICATION NO. : 11/554537
DATED : August 6, 2013
INVENTOR(S) : Timothy Beerling et al.

Page 1 of 1

It is certified that error appears in the above-identified patent and that said Letters Patent is hereby corrected as shown below:

In the Claims:

In column 4, line 67, in claim 1, delete "alone" and insert -- along --, therefor.

Signed and Sealed this
Twenty-second Day of October, 2013

Teresa Stanek Rea
*Deputy Director of the United States Patent and Trademark Office*